(12) United States Patent
Elsesser et al.

(10) Patent No.: US 9,707,374 B2
(45) Date of Patent: Jul. 18, 2017

(54) INFUSION SYSTEM HAVING FILTRATION DEVICE AND METHOD

(75) Inventors: James Elsesser, Bloomington, IN (US); Therese J. O'Day, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 717 days.

(21) Appl. No.: 13/411,953

(22) Filed: Mar. 5, 2012

(65) Prior Publication Data

US 2012/0238967 A1 Sep. 20, 2012

Related U.S. Application Data

(60) Provisional application No. 61/452,343, filed on Mar. 14, 2011.

(51) Int. Cl.
*A61M 25/14* (2006.01)
*A61F 2/01* (2006.01)
(Continued)

(52) U.S. Cl.
CPC .......... *A61M 25/007* (2013.01); *A61F 2/013* (2013.01); *A61F 2002/015* (2013.01);
(Continued)

(58) Field of Classification Search
CPC .......... A61M 25/007; A61M 25/0082; A61M 2025/0175; A61M 2025/09116; A61M 2025/1095–2025/1097; A61F 2002/015
(Continued)

(56) References Cited

U.S. PATENT DOCUMENTS 4,921,484 A * 5/1990 Hillstead .............. A61M 25/10 604/104
5,034,001 A * 7/1991 Garrison ................. A61F 2/95 604/104

(Continued)

FOREIGN PATENT DOCUMENTS

| WO | 9939648 | 8/1999 |
| WO | 0010471 | 3/2000 |
| WO | 02064012 | 8/2002 |

OTHER PUBLICATIONS

Genesis Medical Interventional, F.A.S.T. Funnel Catheter, document, published prior to Mar. 14, 2011, 4 pages.

(Continued)

*Primary Examiner* — Imani Hayman
*Assistant Examiner* — Jenna Zhang
(74) *Attorney, Agent, or Firm* — Liell & McNeil

(57) ABSTRACT

An infusion system includes an infusion catheter defining a fluid passage extending between a proximal catheter end and a distal catheter end, and having a plurality of infusion ports in communication with the fluid passage and defining an infusion zone. A filtration device is provided which may be retrofitted upon the infusion catheter and includes a filter sleeve coupled to a slidable control sleeve. The filter sleeve is deformable between a first configuration having a radially contracted footprint and a second configuration having a radially expanded footprint, responsive to sliding the control sleeve over the infusion catheter such that the deformable filter sleeve buckles outwardly from the infusion catheter.

12 Claims, 3 Drawing Sheets

(51) Int. Cl.
  *A61M 25/00* (2006.01)
  *A61M 25/01* (2006.01)
  *A61M 25/09* (2006.01)
(52) U.S. Cl.
  CPC . *A61F 2002/018* (2013.01); *A61F 2230/0006* (2013.01); *A61F 2230/0069* (2013.01); *A61F 2230/0076* (2013.01); *A61M 25/0082* (2013.01); *A61M 2025/0175* (2013.01); *A61M 2025/09116* (2013.01)
(58) Field of Classification Search
  USPC ............ 606/200, 198; 623/1.11; 604/509, 604/104–109
  See application file for complete search history.

(56) References Cited

U.S. PATENT DOCUMENTS

| | | | |
|---|---|---|---|
| 6,179,860 B1 | 1/2001 | Fulton, III et al. | |
| 6,221,006 B1 | 4/2001 | Dubrul et al. | |
| 6,238,412 B1 | 5/2001 | Dubrul et al. | |
| 6,258,115 B1 | 7/2001 | Dubrul | |
| 6,325,816 B1 | 12/2001 | Fulton, III et al. | |
| 6,409,742 B1 | 6/2002 | Fulton, III et al. | |
| 6,485,500 B1* | 11/2002 | Kokish | A61M 25/104 604/101.01 |
| 6,602,265 B2 | 8/2003 | Dubrul et al. | |
| 6,635,068 B1 | 10/2003 | Dubrul et al. | |
| 6,695,858 B1 | 2/2004 | Dubrul et al. | |
| 6,706,055 B2* | 3/2004 | Douk | A61B 17/12022 606/200 |
| 6,758,855 B2 | 7/2004 | Fulton, III et al. | |
| 6,761,727 B1* | 7/2004 | Ladd | A61B 17/221 606/108 |
| 6,911,036 B2 | 6/2005 | Douk et al. | |
| 7,011,654 B2 | 3/2006 | Dubrul et al. | |
| 7,354,445 B2 | 4/2008 | Nicholson et al. | |
| 7,371,248 B2 | 5/2008 | Dapolito et al. | |
| 7,399,308 B2 | 7/2008 | Borillo et al. | |
| 7,846,175 B2 | 12/2010 | Bonnette et al. | |
| 2002/0111648 A1* | 8/2002 | Kusleika | A61F 2/01 606/200 |
| 2002/0123720 A1* | 9/2002 | Kusleika | A61F 2/01 604/108 |
| 2003/0097114 A1 | 5/2003 | Ouriel et al. | |
| 2003/0150821 A1* | 8/2003 | Bates | A61F 2/01 210/767 |
| 2003/0187475 A1* | 10/2003 | Tsugita | A61F 2/01 606/200 |
| 2004/0199202 A1 | 10/2004 | Dubrul et al. | |
| 2007/0073332 A1 | 3/2007 | Miller et al. | |
| 2007/0208367 A1* | 9/2007 | Fiorella | A61B 17/22 606/198 |
| 2010/0036481 A1 | 2/2010 | Dubrul et al. | |
| 2010/0114113 A1 | 5/2010 | Dubrul et al. | |
| 2010/0286722 A1* | 11/2010 | Rizk | A61F 2/013 606/200 |
| 2011/0040319 A1* | 2/2011 | Fulton, III | A61B 17/22 606/194 |
| 2011/0160742 A1* | 6/2011 | Ferrera | A61B 17/221 606/127 |
| 2011/0213403 A1* | 9/2011 | Aboytes | A61F 2/013 606/194 |
| 2016/0135836 A1* | 5/2016 | Fulton, III | A61B 17/32072 606/159 |

OTHER PUBLICATIONS

Kensey Nash, ThromCat(R) XT(TM) Thrombectomy Catheter System, news release, Jun. 23, 2009, 2 pages, http://salesandmarketingnetwork.com.

Genesis Medical Interventional, 510(lk) Summary for the Genesis Medical Interventional, Attachment 19, news release, Jul. 19, 2004, 2 pages, http://www.evtoday.com.

* cited by examiner

ND METHOD

RELATION TO OTHER PATENT APPLICATION

This application claims priority to provisional patent application 61/452,343, filed Mar. 14, 2011 with the same title.

TECHNICAL FIELD

The present disclosure relates generally to infusion systems, and relates more particularly to a filtration device for percutaneous infusion procedures, having a filter sleeve deformable between radially contracted and radially expanded configurations.

BACKGROUND

Devices known as infusion catheters are commonly used to deliver a therapeutic treatment fluid such as a thrombolytic agent to a clot or other undesired tissue within a vein or artery in a patient. A wide variety of infusion catheter designs are known and commercially available. One conventional design includes a longitudinally extending fluid lumen within an infusion catheter body which connects a supply of treatment fluid positioned outside of the patient with an intraluminal space such as a vein or artery by way of effusion ports formed in the catheter body.

During certain infusion procedures, and notably procedures where a thrombolytic agent is used to dissolve or break up clot material within a vein or artery, pieces of the clot may become dislodged, potentially causing complications in a well known manner. A variety of filtration mechanisms are used to capture pieces of clot material or "emboli" such that the material can be removed from the patient, dissolved by a thrombolytic agent, or otherwise prevented from migrating to other regions of the patient's body.

In venous infusion procedures, a common filtration strategy involves implanting a filter within the vena cava of the patient, such that any emboli which migrate from an infusion site are prevented from entering the patient's heart or lungs. Vena cava filters of many different designs have been used successfully for years. One downside to their use, however, is that a semi-permanent filter is implanted within the patient, and typically must at some point be removed. This necessitates a subsequent interventional procedure. Other filter techniques utilize filters placed close to the infusion site, and often designed as integral parts of the infusion catheter itself or other interventional instruments. These conventional techniques too have their disadvantages.

SUMMARY OF THE DISCLOSURE

In one aspect, a filtration device for use in an infusion procedure includes a rigid control sleeve defining a longitudinal axis and including a proximal control sleeve end, a distal control sleeve end, and a handle coupled with the proximal control sleeve end. The filtration device further includes a deformable filter sleeve coupled to the rigid control sleeve and positioned coaxially therewith, the deformable filter sleeve having an axial length, and a radial footprint inversely correlated with the axial length. The filtration device further includes a stop collar coupled to the deformable filter sleeve and positioned at a spacing distance from the rigid control sleeve. The axial length of the deformable filter sleeve is defined by the spacing distance such that moving the rigid control sleeve toward the stop collar responsively expands the radial footprint.

In another aspect, an infusion system includes an infusion catheter defining a fluid passage extending between a proximal catheter end and a distal catheter end, and further having a plurality of infusion ports in communication with the fluid passage and defining an infusion zone. The infusion system further includes a filtration device retrofitted upon the infusion catheter and including a filter sleeve coupled to a slidable control sleeve. The filter sleeve is coupled to the infusion catheter proximal to the infusion zone, and is deformable between a first configuration having a radially contracted footprint and a second configuration having a radially expanded footprint, responsive to sliding the control sleeve over the infusion catheter.

In still another aspect, a method of performing an infusion procedure on a patient includes sliding a filtration device over an infusion catheter to a position at which a deformable filter sleeve of the filtration device is positioned proximal to a distal infusion zone of the infusion catheter. The method further includes coupling the deformable filter sleeve to the infusion catheter, and expanding a radial footprint of the deformable filter sleeve at least in part by sliding a rigid control sleeve of the filtration device in a distal direction over the infusion catheter.

DETAILED DESCRIPTION

Figure 1:
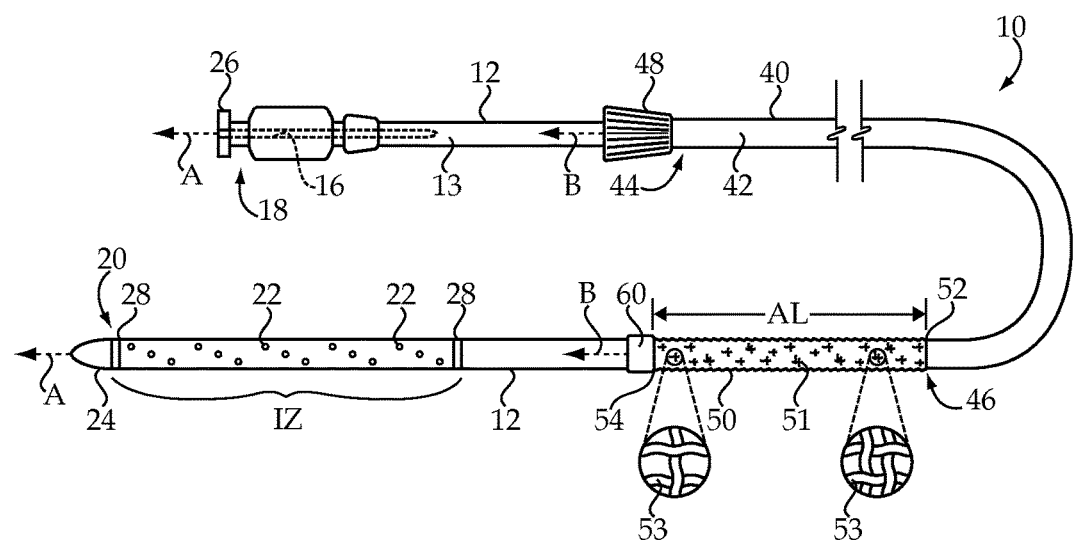
FIG. 1 is a side diagrammatic view of an infusion system, including detailed enlargements, according to one embodiment.

Referring to FIG. 1, there is shown an infusion system 10 according to one embodiment. Infusion system 10 includes an infusion catheter 12 defining a fluid passage 16 extending between a proximal catheter end 18 and a distal catheter end 20. A plurality of infusion ports 22 are formed in infusion catheter 12 and are in communication with fluid passage 16. Infusion ports 22 define an infusion zone IZ extending between radiopaque markers 28, and positioned adjacent a distal catheter tip 24 which includes a distally narrowing taper. A fitting 26 is coupled with proximal catheter end 18 and configured to connect with other components used in performing an infusion procedure on a patient, as further described herein.

Infusion catheter 12 may include an elongate catheter body 13 defining a longitudinal axis A. A filtration device 40 is positioned upon elongate catheter body 13, and may be retrofitted upon infusion catheter 12 in a manner further described herein. In other words, filtration device 40 defines a through passage to receive infusion catheter 12. Filtration device 40 may include a rigid control sleeve 42 defining a longitudinal axis B collinear with longitudinal axis A. Rigid control sleeve 42 may include a proximal control sleeve end 44, a distal control sleeve end 46, and a handle 48 coupled with proximal control sleeve end 44. In the embodiment shown, infusion catheter 12 extends through handle 48.

Filtration device 40 may further include a deformable filter sleeve 50 coupled to control sleeve 42 and positioned coaxially therewith, and located upon catheter 12 proximal to distal infusion zone IZ. Deformable filter sleeve 50 includes an axial length AL, and a radial footprint inversely correlated with axial length AL. A stop collar 60 is coupled to filter sleeve 50 and positioned at a spacing distance from control sleeve 42. Axial length AL is defined by the spacing distance such that moving control sleeve 42 toward or away from stop collar 60 adjusts axial length AL and responsively changes the radial footprint of filter sleeve 50. In particular, sliding filter sleeve 50 toward stop collar 60 reduces axial length AL and expands the radial footprint, and vice versa, the significance of which will be apparent from the following description.

Filter sleeve 50 may further include a filter medium 51, and in one embodiment may be formed entirely of filter medium 51. Filter medium 51 may include a metallic filtration medium such as a metallic mesh including a plurality of metal fibers 53, shown by way of detailed enlargements in FIG. 1. Filtration medium 51 may be formed by weaving, braiding, knitting, welding, or any other suitable methodology for forming a metallic mesh filtration medium from a plurality of metallic fibers.

Figure 2:
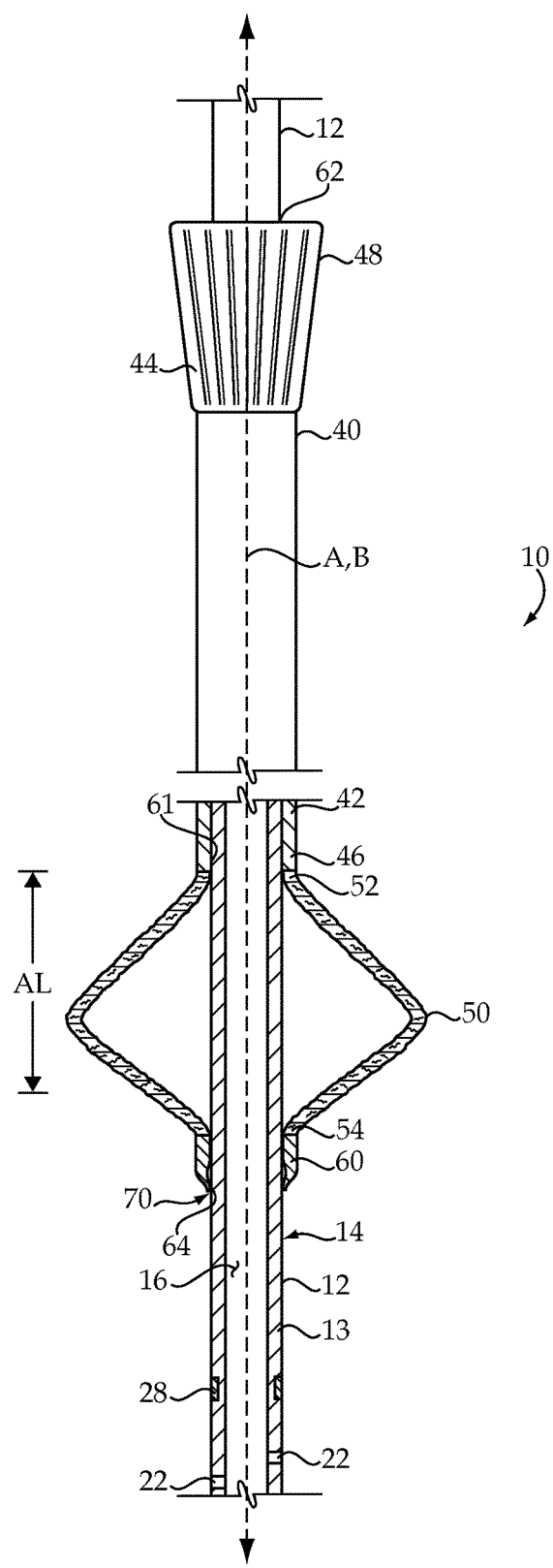
FIG. 2 is a partially sectioned side diagrammatic view of a portion of the infusion system of FIG. 1.

Referring also now to FIG. 2, there is shown a partially sectioned side diagrammatic view of a portion of infusion system 10 of FIG. 1. It will be recalled that axial length AL of filter sleeve 50 may be defined by a spacing distance in an axial direction between control sleeve 42 and stop collar 60. In FIG. 1, filtration device 40 is shown in a first configuration as might be used for accessing a body lumen such as a vein or artery in a patient. In the first configuration, filtration device 40 includes an expanded axial length and a contracted radial footprint. Filtration device 40 may be adjustable to a second configuration having a contracted axial length and an expanded radial footprint, approximately as shown in FIG. 2, via moving control sleeve 42 toward stop collar 60. Stop collar 60 may be irreversibly attached to a distal filter sleeve end 54, and reversibly attached to infusion catheter 12. The term "irreversibly attached" should be understood to mean that stop collar 60 and filter sleeve 50 cannot be detached from one another without damaging or rendering unusable one or both of the respective components. The term "reversibly attached," in contrast, should be understood to mean that stop collar 60 and catheter 12 may be detached from one another without damaging or rendering unusable one or both of the respective components. In one embodiment, stop collar 60 may include a one-way stop collar which is configured to slide over an outer surface 14 of elongate catheter body 13 in one direction with a relatively lesser resistance, but experiences a relatively greater resistance when slid over outer surface 14 in an opposite direction, as further described herein.

In the embodiment shown, distal filter sleeve end 54 includes an open end centered on axes A and B, whereas an opposite proximal filter sleeve end 52 also includes an open end centered on axes A and B. Proximal control sleeve end 44, and distal control sleeve end 46 may each also include an open end such that a passage 61 extends through filtration device 40 from a first open passage end 62 located in proximal control sleeve end 44 to a second open passage end 64 located in stop collar 60. Providing a passage extending all the way through filtration device 40 in the manner shown in FIGS. 1 and 2 enables filtration device 40 to be slid over catheter 12 for use in an infusion procedure on a patient, as further described herein.

It will be recalled that filter sleeve 50 may be deformable relative to control sleeve 42. In general terms, this may be understood to mean that a relatively lesser magnitude of force is required to buckle or deform filter sleeve 50 than is required to buckle or deform control sleeve 42. In practical terms, this may be understood to mean that when filtration device 40 is positioned upon and coupled with infusion catheter 12, a clinician can manipulate the axial length and thus radial footprint of filter sleeve 50 by pushing or pulling control sleeve 42 in axial directions from a location outside the patient. As alluded to above, a clinician may push control sleeve 42 towards stop collar 60 to expand filter sleeve 50 radially outward from its first configuration to its second configuration. When it is desirable to collapse filter sleeve 50, in other words return filtration device 40 to the first configuration, the clinician may pull control sleeve 42 in an axial direction away from stop collar 60.

In one embodiment, stop collar 60 may resist sliding over elongate catheter body 13 by way of a friction coupling 70 via contact between an annular inner surface of stop collar 60 and an outer surface of the elongate catheter body 13. As noted above, stop collar 60 may include a one-way stop collar such that a first coefficient of slip resistance between stop collar 60 and elongate catheter body 13 exists in a first direction, and a second coefficient of slip resistance exists in a second direction. In one embodiment, the first coefficient may define a first slip resistance force having a greater value such that it is relatively more difficult to push stop collar 60 in a proximal to distal direction along outer surface 14 of catheter body 13. The second coefficient may define a second slip resistance force having a medium value, such that it is moderately difficult to push stop collar 60 in an opposite direction along outer surface 14. Filter sleeve 50 may include a coefficient of buckling resistance defining a buckling resistance force having a lower value. Another way to understand these principles is that it can be expected to be relatively more difficult to push stop collar 60 in a distal direction than in a proximal direction when friction coupling 70 is established between stop collar 60 and catheter body 13. The forces required to slide stop collar 60 in either of a proximal direction or a distal direction, however, may be greater than the force required to buckle filter sleeve 50 to adjust filtration device 40 from its first configuration to its second configuration. Similarly, the force required to radially contract filter sleeve 50, returning from the second configuration to the first configuration, may be less than the forces required to slide stop collar 60 in either of a proximal or distal direction. These properties thus allow stop collar 60 to serve as a mechanical stop for enabling adjustments of filter sleeve 50, but also facilitating slidably positioning filtration device 40 for service upon catheter 12. In one practical implementation strategy, stop collar 60 may be shaped such that it "bites" into material of catheter body 13 when pushed in one direction along catheter 12, but does not bite into the material or does so only to a lesser degree when pushed in an opposite direction.

It will be recalled that the radial footprint of filter sleeve 50 may be inversely correlated with axial length AL. The radial footprint may be understood as an area defined by filter sleeve 50 in a plane oriented normal to and intersecting longitudinal axis B. Thus, were filter sleeve 50 to be viewed end on in its first configuration, the area defined by the radial footprint would appear relatively small. When viewed end on, looking down axis B, in the second, expanded configuration, the subject area would appear relatively large. It may further be noted that the radial footprint of filter sleeve 50 may be substantially the same in the first configuration regardless of axial location. In other words, in the first configuration the radial footprint may be axially uniform approximately as shown in FIG. 1. In the second configuration, the radial footprint of filter sleeve 50 may be axially non-uniform, such that the actual radial footprint would vary depending upon what axial location is being considered.

INDUSTRIAL APPLICABILITY

Figure 3:
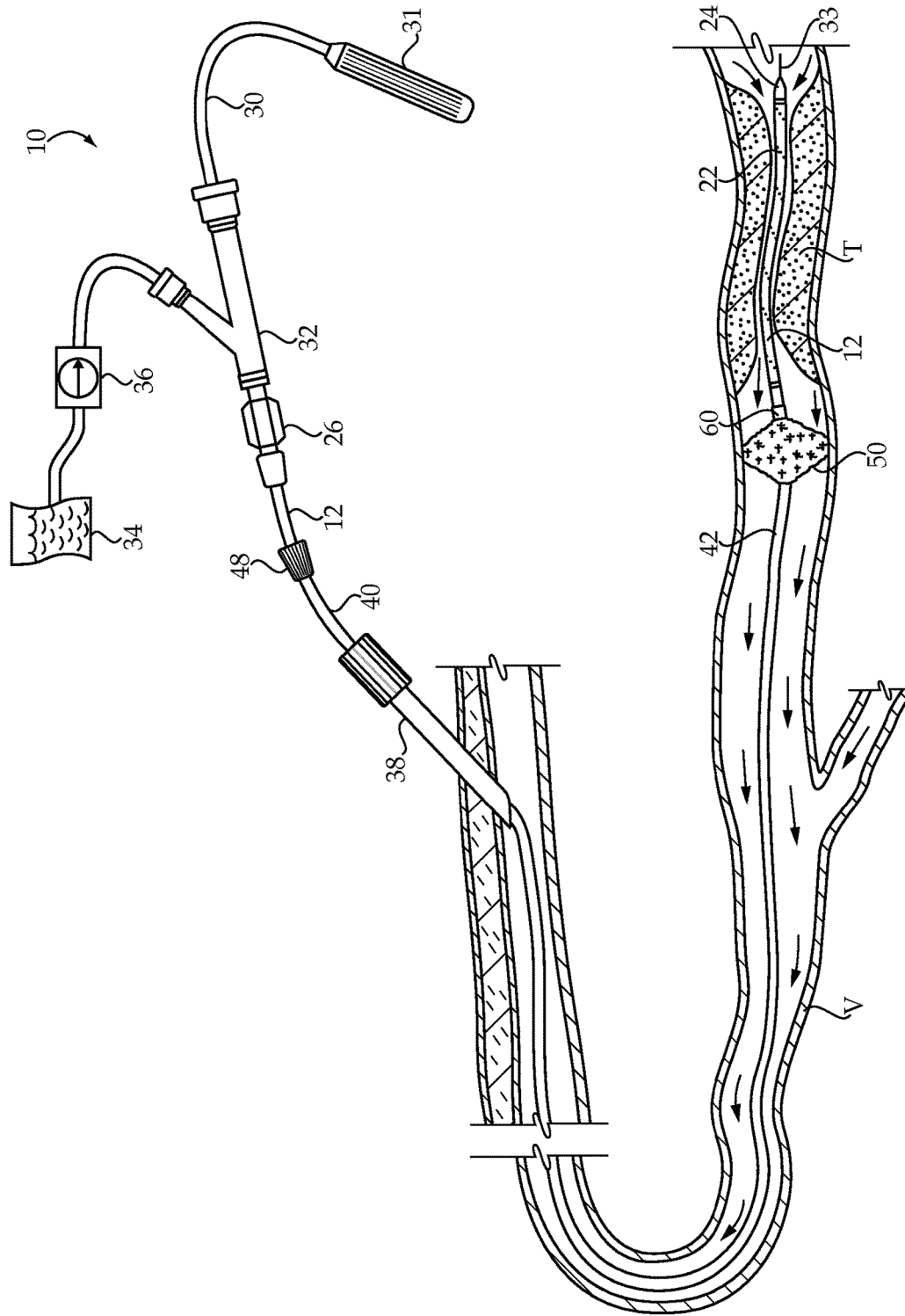
FIG. 3 is a side diagrammatic view of the infusion system of FIGS. 1 and 2, positioned for performing an infusion procedure on a patient.

Referring to the drawings generally, but in particular now to FIG. 3, there is shown infusion system 10 assembled and positioned for use in performing an infusion procedure on a patient. Infusion catheter 12 has been placed by way of a wire guide 30 at a target location within a vascular lumen V of the patient. In one application, vascular lumen is a vascular lumen of a vein. A distal tip 33 of wire guide 30 is shown extending out of distal catheter tip 24, and infusion ports 22 are positioned to effuse a liquid treatment agent such as a thrombolytic agent into vascular lumen V in the vicinity of a thrombus T. It may be noted that infusion catheter 12 has been advanced through vascular lumen V in a direction retrograde to a flow of blood through vascular lumen V as indicated by arrows within vascular lumen V. A Y-fitting 32 is coupled with infusion catheter 12, and an infusion pump 36 supplies the liquid treatment agent from a fluid reservoir 34 into catheter 12 in a conventional manner. An introducer sheath 38 provides an access pathway through the patient's skin and into vascular lumen V. Wire guide 30 is shown equipped with a handle 31 for manipulating wire guide 30 in a conventional manner. Filtration device 40 has been positioned upon catheter 12 and advanced through vascular lumen V contemporaneously herewith. Filtration device 40 is shown in its second, deployed configuration, and has been expanded radially outwardly from catheter 12 such that it contacts an inner wall of vascular lumen V.

As noted above, filtration device 40 may be retrofitted upon infusion catheter 12. In one practical implementation strategy, retrofitting of filtration device 40 upon infusion catheter 12 may include sliding filtration device 40 over infusion catheter 12 outside of the patient, to a position at which filter sleeve 50 is positioned proximal to distal infusion zone IZ of catheter 12. In particular, filtration device 40 may be slid in a proximal direction by first inserting distal catheter tip 24 into open passage end 62 of passage 61 in handle 48. During sliding filtration device 40 over infusion catheter 12, stop collar 60 may be relatively easily slid to a location proximal to distal infusion zone IZ, and establishing frictional coupling 70. Once positioned appropriately, infusion catheter 12 and filtration device 40 may be advanced together over wire guide 30 to the target location as described herein. Upon positioning filtration device 40 and infusion catheter 12 at the target location the clinician may, by way of manipulating handle 48, slide control sleeve 42 towards stop collar 60 to axially shorten filter sleeve 50 and responsively expand the radial footprint thereof. Frictional coupling 70 between stop collar 60 and infusion catheter 12 will resist sliding of filter sleeve 50, and allow the axial force applied to filter sleeve 50 to buckle filter sleeve 50 outwardly and into conformity with an inner wall of vascular lumen V.

With infusion system 10 deployed approximately as shown in FIG. 3, filter sleeve 50 can trap emboli or other particulates flowing through vascular lumen V, such as emboli generated via the action of liquid thrombolytic agent. In some instances, emboli may be trapped and retained within filter sleeve 50 such that infused thrombolytic agent can travel with a flow of blood through filter sleeve 50 and dissolve the trapped emboli. In other instances, the trapped emboli may be retained within filter sleeve 50, in particular between and among fibers 53, such that upon collapsing filter sleeve 50 and returning filtration device 40 to its first configuration, the trapped emboli may be removed with device 40 as it is removed from the patient. In one practical implementation strategy, filter medium 51 may include a uniform porosity. In another practical implementation strategy, filter medium 51 may include a distally increasing porosity. It may be noted from FIG. 1 that fibers 53 in the proximally located detailed enlargement are spaced relatively closer to one another than are fibers 53 shown in the distally located detailed enlargement. It may further be noted from FIG. 1 that fibers 53 are shown in contact with one another. When filter sleeve 50 is radially expanded upon adjusting filtration device 40 to the second configuration, fibers 53 may slide against one another but generally remain in contact with one another even after reaching the radially expanded configuration conforming with the inner wall of a vascular lumen.

Certain known filtration systems utilize a filter mechanism formed integrally or as a component of an infusion catheter. While such designs have various applications, they tend to be relatively expensive to manufacture. Moreover, it may actually be desirable to place a filter at a location other than that which can be readily reached using a combination infusion catheter and filter, or upon preparing to perform an infusion procedure it might be concluded that it is not necessary to use a filter at all. In other known techniques, particularly as applied in the venous system, a separate filter may be placed such as in the vena cava to prevent emboli from passing into the heart. This technique adds expense and time to a procedure and leaves an implant at least temporarily within the patient. The present disclosure provides for an optional treatment strategy, whereby a clinician may choose to retrofit a filtration device upon an infusion catheter if such is desired. The filtration devices discussed herein can provide a temporary filter positionable downstream an infusion site if desired, but which can be readily removed upon withdrawing the infusion catheter at the conclusion of the procedure. Accordingly, a relatively inexpensive, separate device can be added to a variety of different existing infusion catheters as needed without the need to purchase potentially unnecessary equipment, or implant a more permanent device.

In one practical implementation strategy, filtration device 40 may be formed by extruding material of control sleeve 42, and bonding handle 48 and filter sleeve 50 to control sleeve ends 44 and 46 via an adhesive, fusing or softened or melted materials, or any other suitable technique. Stop collar 60 may be bonded to filter sleeve 50 prior to or subsequent to bonding filter sleeve 50 to control sleeve 42. In an alternative implementation strategy, the entirety of an axial length of a filtration device, or nearly the entirety, may be formed from a filtration medium such as medium 51, but a portion coated with a suitable rigid material such as heat shrunk polymeric material, to result in a relatively more rigid control segment and a relatively less rigid filter segment, as described herein.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims.

What is claimed is:

1. An infusion system comprising:
   an infusion catheter defining a fluid passage extending between a proximal catheter end and a distal catheter end, and further having a plurality of infusion ports in communication with the fluid passage and defining an infusion zone; and
   a filtration device retrofitted upon the infusion catheter and including a control sleeve defining a longitudinal axis and including a proximal control sleeve end, a distal control sleeve end, and a handle coupled with, and bonded to, the proximal control sleeve end and having a centerline coaxial with the longitudinal axis; a deformable filter sleeve attached directly to the control sleeve and positioned coaxially therewith, the deformable filter sleeve having an axial length, and a radial footprint inversely correlated with the axial length; and, a stop collar that includes an annular inner surface in contact with an outer surface of the infusion catheter to form a friction coupling, and the stop collar being attached directly to the deformable filter sleeve and positioned at a spacing distance from the control sleeve, and the axial length of the deformable filter sleeve being defined by the spacing distance such that moving the control sleeve with the handle toward the stop collar responsively expands the radial footprint, the deformable filter sleeve includes a mesh extending from the control sleeve to the stop collar, the filter sleeve further being coupled to the infusion catheter proximal to the infusion zone, and being deformable between a first configuration having a radially contracted footprint and a second configuration having a radially expanded footprint, responsive to sliding the control sleeve over the infusion catheter; and
   the infusion catheter extending through the handle coaxial with the centerline of the handle.

2. The infusion system of claim 1 wherein the filter sleeve is coupled to the infusion catheter by way of the stop collar, the stop collar being reversibly attached to the infusion catheter and irreversibly attached to the filter sleeve.

3. The infusion system of claim 2 further comprising a friction coupling between the stop collar and the infusion catheter, and having a first coefficient of slip resistance in a first direction, and a second coefficient of slip resistance in a second direction.

4. The infusion system of claim 3 wherein the first coefficient defines a first slip resistance force having a greater value, the second coefficient defines a second slip resistance force having a medium value, and the filter sleeve includes a coefficient of buckling resistance defining a buckling resistance force having a lower value.

5. The infusion system of claim 2 wherein the filter sleeve includes an open proximal end and an open distal end, each of the open proximal and distal ends being centered on the longitudinal axis.

6. The infusion system of claim 5 wherein the filter sleeve includes an expanded axial length in the first configuration, and a contracted axial length in the second configuration, and wherein the filter sleeve is in the first configuration and is deformable to the second configuration in response to sliding the control sleeve over the infusion catheter towards the stop collar.

7. The infusion system of claim 6 wherein the radially contracted footprint is axially uniform and the radially expanded footprint is axially non-uniform.

8. The infusion system of claim 5 wherein the filter sleeve includes a metallic filtration medium having a plurality of metal fibers contacting one another in each of the first and second configurations.

9. A method of performing an infusion procedure on a patient with a filtration device that includes a control sleeve defining a longitudinal axis and including a proximal control sleeve end, a distal control sleeve end, and a handle coupled with, and bonded to, the proximal control sleeve end and having a centerline coaxial with the longitudinal axis; a deformable filter sleeve attached directly to the control sleeve and positioned coaxially therewith, the deformable filter sleeve having an axial length, and a radial footprint inversely correlated with the axial length; a stop collar attached directly to the deformable filter sleeve and positioned at a spacing distance from the control sleeve, and the axial length of the deformable filter sleeve being defined by the spacing distance such that moving the control sleeve toward the stop collar responsively expands the radial footprint; and the filtration device defines a through passage sized to receive an infusion catheter, and the deformable filter sleeve includes a mesh extending from the control sleeve to the stop collar, and the stop collar includes an annular inner surface for contacting, and forming a friction coupling with, an outer surface of the infusion catheter received therethrough, the method comprising the steps of:
   sliding the filtration device over the infusion catheter to a position at which the deformable filter sleeve of the filtration device is positioned proximal to a distal infusion zone of the infusion catheter and the infusion catheter extends through the handle coaxial with the centerline;
   coupling the deformable filter sleeve to the infusion catheter; and
   expanding the radial footprint of the deformable filter sleeve at least in part by sliding the control sleeve of the filtration device with the handle in a distal direction over the infusion catheter.

10. The method of claim 9 wherein the step of sliding further includes sliding the filtration device in a proximal direction over the infusion catheter, prior to placing the infusion catheter within the patient.

11. The method of claim 10 further comprising a step of advancing the infusion catheter and the filtration device through a vein of the patient in a direction retrograde to a direction of blood flow through the vein.

12. The method of claim 11 wherein the step of coupling further includes establishing a frictional coupling between the annular inner surface of the stop collar and the infusion catheter; and
   the stop collar is a one-way stop collar with different coefficients of friction for movement on the infusion catheter in opposite directions along the longitudinal axis.

* * * * *